(12) United States Patent
Chon et al.

(10) Patent No.: US 8,718,753 B2
(45) Date of Patent: May 6, 2014

(54) MOTION AND NOISE ARTIFACT DETECTION FOR ECG DATA

(76) Inventors: Ki H. Chon, Worcester, MA (US);
Jinseok Lee, Worcester, MA (US)

(*) Notice: Subject to any disclaimer, the term of this patent is extended or adjusted under 35 U.S.C. 154(b) by 0 days.

(21) Appl. No.: 13/823,812

(22) PCT Filed: Oct. 12, 2011

(86) PCT No.: PCT/US2011/055989
§ 371 (c)(1),
(2), (4) Date: Mar. 15, 2013

(87) PCT Pub. No.: WO2012/051320
PCT Pub. Date: Apr. 19, 2012

(65) Prior Publication Data
US 2013/0190638 A1  Jul. 25, 2013

Related U.S. Application Data

(60) Provisional application No. 61/392,261, filed on Oct. 12, 2010, provisional application No. 61/436,408, filed on Jan. 26, 2011.

(51) Int. Cl.
*A61B 5/04* (2006.01)
(52) U.S. Cl.
USPC ............................................. 600/521
(58) Field of Classification Search
USPC ............................................. 600/521
See application file for complete search history.

(56) References Cited

U.S. PATENT DOCUMENTS

| 2006/0025824 | A1 | 2/2006 | Freeman et al. |
| 2008/0269628 | A1 | 10/2008 | Koertge et al. |
| 2009/0069703 | A1 | 3/2009 | Takla et al. |
| 2011/0158259 | A1* | 6/2011 | Chen et al. ............. 370/482 |

OTHER PUBLICATIONS

Chon, K. H. et al., Estimation of Respiratory Rate From Photoplethysmogram Data Using Time-Frequency Spectral Estimation, IEEE Transactions on Biomedical Engineering, Aug. 2009, 2054-2063, vol. 56, No. 8.
Lu, S. et al., A New Algorithm for Linear and Nonlinear ARMA Model Parameter Estimation Using Affine Geometry, IEEE Transactions on Biomedical Engineering, Oct. 2001, 1116-1124, vol. 48, No. 10.

(Continued)

*Primary Examiner* — Robert N Wieland
(74) *Attorney, Agent, or Firm* — Burns & Levinson LLP; Jacob N. Erlich; Orlando Lopez

(57) ABSTRACT

Technologies are provided herein for real-time detection of motion and noise (MN) artifacts in electrocardiogram signals recorded by electrocardiography devices. Specifically, the present disclosure provides techniques for increasing the accuracy of identifying paroxysmal atrial fibrillation (AF) rhythms, which are often measured via such devices. According to aspects of the present disclosure, a method for detecting MN artifacts in an electrocardiogram (ECG) recording includes receiving an ECG segment and decomposing the received ECG segment into a sum of intrinsic mode functions. The intrinsic mode functions associated with MN artifacts present within the ECG segment are then isolated. The method further includes determining randomness and variability characteristic values associated with the isolated intrinsic mode functions and comparing the randomness and variability characteristic values to threshold randomness and variability characteristic values. If the randomness and variability characteristic values exceed the threshold characteristic values, the ECG signal is determined to include MN artifacts.

26 Claims, 13 Drawing Sheets

(56) References Cited

OTHER PUBLICATIONS

Xiao, X. et al., A Model Order Selection Criterion With Applications to Cardio-Respiratory-Renal Systems, IEEE Transactions on Biomedical Engineering, Mar. 2005, 445-453, vol. 52, No. 3.

Zou, R. et al., Robust Algorithm for Estimation of Time-Varying Transfer Functions IEEE Transactions on Biomedical Engineering, Feb. 2004, 219-228, vol. 51, No. 2.

Lee, J. et al., An Autoregressive Model-Based Particle Filtering Algorithms for Extraction of Respiratory Rates as High as 90 Breaths Per Minute From Pulse Oximeter IEEE Transactions on Biomedical Engineering Sep. 2010, 2158-2167, vol. 57, No. 9.

Kotecha, J. H. et al., Gaussian Particle Filtering, IEEE Transactions on Signal Processing, Oct. 2003, 2592-2601, vol. 51, No. 10.

Zhong, Y. et al., Representation of Time-Varying Nonlinear Systems With Time-Varying Principal Dynamic Modes IEEE Transactions on Biomedical Engineering, Nov. 2007, 1983—vol. 54, No. 11.

Arulampalam, M.S. et al., A Tutorial on Particle Filters for Online Nonlinear/Non-Gaussian Bayesian Tracking IEEE Transactions on Signal Processing, Feb. 2002, 174-188, vol. 50, No. 2.

International Search Report and Written Opinion dated Apr. 10, 2012 for PCT/US11/55989.

International Preliminary Report on Patentability dated Apr. 25, 2013 for PCT/US11/55989.

\* cited by examiner

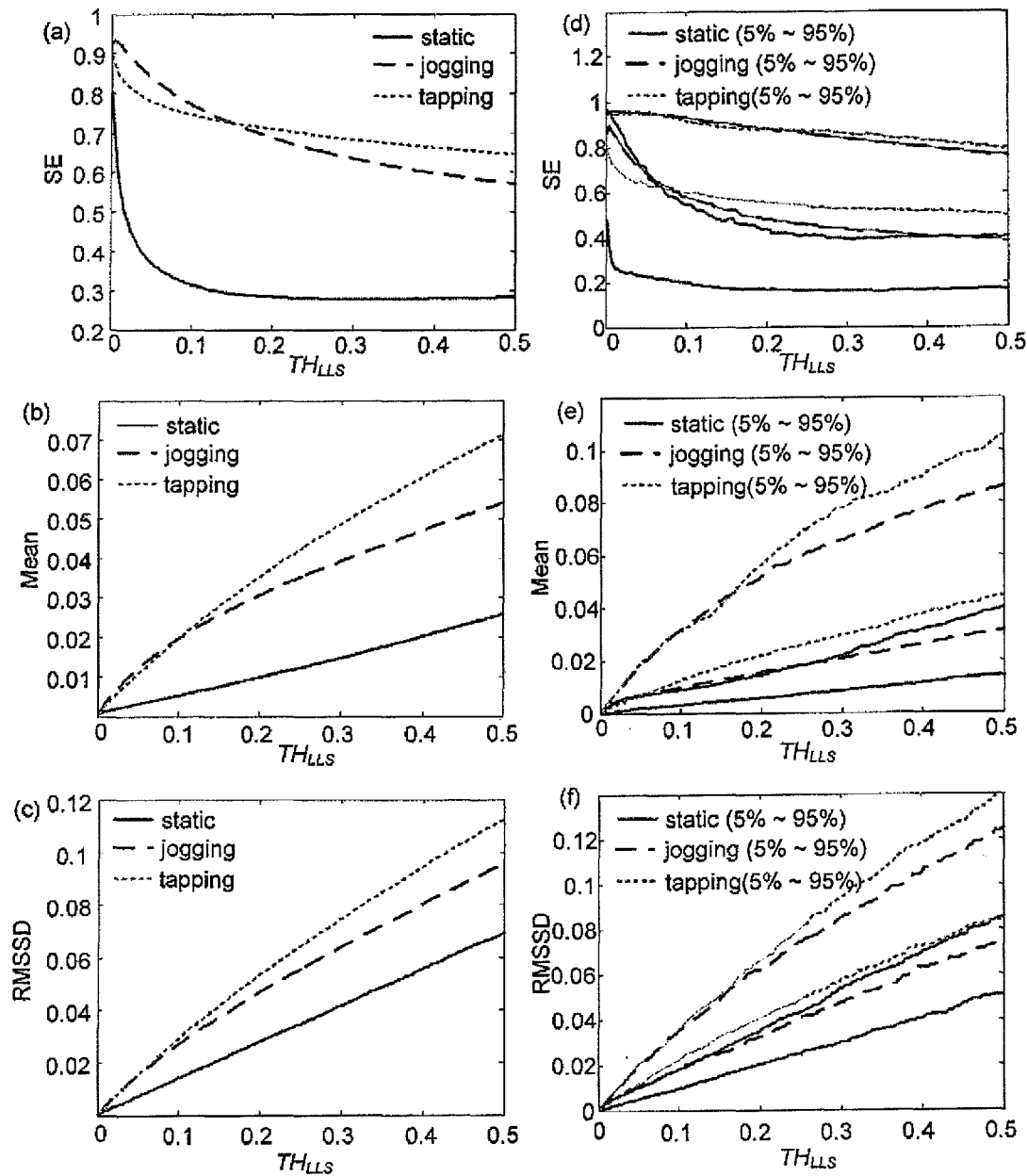
FIGS. 7A-F

MOTION AND NOISE ARTIFACT DETECTION FOR ECG DATA

CROSS-REFERENCE TO RELATED APPLICATIONS

This application is a U.S. national stage application under 35 U.S.C. 371 of co-pending international Application No. PCT/US11/55989 filed on Oct. 12, 2011 and entitled MOTION AND NOISE ARTIFACT DETECTION FOR ECG DATA, which in turn claims priority to U.S., Provisional Patent Application No. 61/392,261 filed on Oct. 12, 2010, and to U.S. Provisional Patent Application No. 61/436,408 filed on Jan. 26, 2011, all of which are incorporated by reference herein in their entirety for all purposes.

STATEMENT REGARDING FEDERALLY SPONSORED RESEARCH OR DEVELOPMENT

This invention was made partially with U.S. Government support from the office of Naval Research under work unit N00014-08-1-0244. The U.S. Government has certain rights in the invention.

BACKGROUND

Electrocardiography is a diagnostic procedure for the detection and diagnosis of heart abnormalities. The electrocardiogram (ECG) signal contains important information that is utilized by physicians for the diagnosis and analysis of heart diseases. So good quality ECG signal plays a vital role for the interpretation and identification of pathological, anatomical and physiological aspects of the whole cardiac muscle. However, the ECG signals are corrupted by noise which severely limit the utility of the recorded ECG signal for medical evaluation. The most common noise presents in the ECG signal is the high frequency noise caused by the forces acting on the electrodes.

An ambulatory electrocardiography device, such as a Holter monitor, is a portable device for monitoring electrical activity of the central nervous system for long periods of time. For many years, such devices have been used to record electrocardiogram signals, which contain important information that is used for the diagnosis and analysis of heart diseases and conditions, such as atrial fibrillation (AF). Use of Holter monitors for extended periods of time is essential given the paroxysmal, often short-lived, and frequently asymptomatic nature of AF. Clinically, monitoring for AF is important because, despite often being paroxysmal and associated with minimal or no symptoms, these arrhythmias are often associated with severely adverse health consequences, including stroke and heart failure. Motion and noise (MN) artifacts are significant during Holter recordings and can lead to false detections of AF. Clinicians have cited MN artifacts in ambulatory monitoring devices as the most common cause of false alarms, loss of signal, and inaccurate readings.

Previous computational efforts have largely relied on MN artifact removal, and some of the popular methods include linear filtering, adaptive filtering, wavelet denoising and Bayesian filtering methods. One main disadvantage of the adaptive filtering methods is that they require a reference signal which is presumed to be correlated in some way with the MN artifacts. The wavelet denoising approach attempts to separate clean and noisy wavelet coefficients, but this approach can be difficult since it requires determination of thresholds. Bayesian filtering requires estimation of optimal parameters using any variant of Kalman filtering methods: extended Kalman filter (EKF), extended Kalman smoother (EKS) and unscented Kalman filter (UKF).

While the above-mentioned signal processing approaches have been applied, they fail to satisfactorily solve problems associated with MN artifacts, and consequently MN artifacts remain a key obstacle to accurate detection of AF and atrial flutter, which is an equally problematic arrhythmia.

Accordingly, there is a need for methods and systems that can separate clean ECG portions from segments with MN artifacts in real time for more accurate diagnosis and treatment of clinically important atrial arrhythmias.

BRIEF SUMMARY

Technologies are provided herein for real-time detection of motion and noise (MN) artifacts in electrocardiogram signals recorded by ambulatory electrocardiography devices. Specifically, the present disclosure provides techniques for increasing the accuracy of identifying paroxysmal atrial fibrillation (AF) rhythms, which are often measured via such devices.

According to aspects of the present disclosure, a method for detecting motion and noise (MN) artifacts in an electrocardiogram (ECG) recording includes receiving an ECG segment and decomposing the received ECG segment into a sum of intrinsic mode functions. The intrinsic mode functions associated with motion and noise artifacts present within the ECG segment are then isolated. The method further includes determining randomness and variability characteristic values associated with the isolated intrinsic mode functions and comparing the randomness and variability characteristic values to threshold randomness and variability characteristic values. If the randomness and variability characteristic values exceed the threshold randomness and variability characteristic values, then the ECG signal is determined to include motion and noise artifacts.

According to other embodiments, a system and computer-readable storage medium for real-time detection of motion and noise artifacts in an ECG signal are disclosed herein. It should be appreciated that the scope of the present disclosure is not limited to the methods, systems and computer-readable storage mediums disclosed herein, but extend to any other implementation of the teachings described herein.

For a better understanding of the present teachings, together with other and further needs thereof, reference is made to the accompanying drawings and detailed description.

BRIEF DESCRIPTION OF THE DRAWINGS

FIGS. 7A-F illustrate average, high 5% and high 95% (bottom 5%) values of Shannon Entropy (SE), mean and RMSSD according to $T_{HLLS}$ for static, jogging, and tapping modes, according to embodiments of the present disclosure;

DETAILED DESCRIPTION

Technologies are provided herein for real-time detection of motion and noise (MN) artifacts in electrocardiogram signals recorded by ambulatory electrocardiography devices. Specifically, the present disclosure provides techniques for increasing the accuracy of identifying paroxysmal atrial fibrillation (AF) rhythms, which are often measured via such devices.

It should be noted that although some embodiments disclosed herein below refer to data received from a Holter monitor, such embodiments are presented only to illustrate the present teachings. It should be understood that the scope of the present disclosure is not limited to such embodiments, but rather extends to implementations that utilize any type of ECG recording device.

As described above, existing AF detection algorithms utilize filtering or signal reconstruction methods that typically result in distorting the location of R-wave peaks, while algorithms using signal reconstruction methods utilize estimation. As a result, such methods adversely affect RR interval duration calculations, which can lead to the incorrect classification of the presence or absence of AF. In contrast, the present disclosure describes technologies that utilize a real-time MN artifact detection algorithm to improve the accuracy of detecting an AF in an ECG signal.

Figure 1:
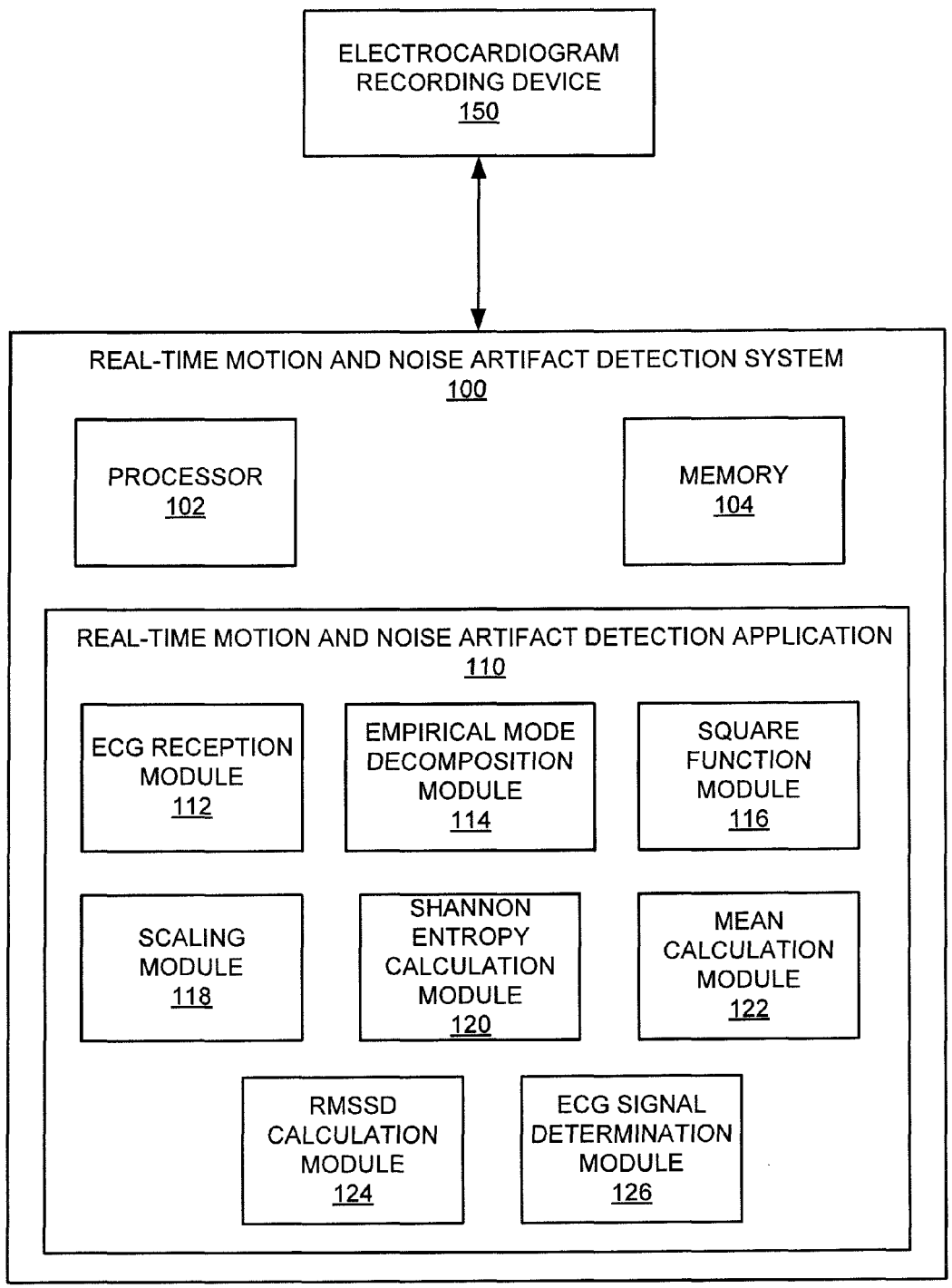
FIG. 1 is a block diagram illustrating a real-time motion and noise artifact detection system according to embodiments of the present disclosure.

Referring now to FIG. 1, a block diagram illustrating a real-time motion and noise (MN) artifact detection system 100 is shown in accordance with various embodiments of the present disclosure. In particular, the real-time MN artifact detection system 100 includes a processor 102, and a memory 104. In addition, the real-time MN artifact detection system 100 also includes a real-time MN artifact detection application 110, which includes one or more software modules, which can be executed by the processor 102. These software modules may perform one or more operations that allow the system 100 to detect MN artifacts from an ECG segment in real-time, and thereby declare a particular ECG signal as noisy if the signal has MN artifacts, or clean if the signal is free from MN artifacts.

The real-time MN artifact detection application 110 may include an ECG segment reception module 112 configured to receive one or more ECG segments from an ECG recording or monitoring device, including but not limited to, a Holter monitor 150. The application 110 further includes an empirical mode decomposition (EMD) module 114 that can decompose an ECG signal into a sum of intrinsic mode functions (IMFs) using empirical mode decomposition. An IMF is defined as a function with equal number of extrema and zero crossings (or at most differed by one) with its envelopes, as defined by all the local maxima and minima, being symmetric with respect to zero. It has been determined that motion and noise artifacts typically lie in the first order intrinsic mode functions corresponding to a decomposed ECG signal.

Given a signal x(t), in various embodiments, EMD can be defined by the following procedure.
1. Identify all extrema of x(t).
2. Interpolate between minima (respectively, maxima) by using a cubic spline and ending up with some envelope $e_{min}(t)$ (respectively, $e_{max}(t)$).
3. Compute the mean $m(t)=(e_{min}(t)+e_{max}(t))/2$.
4. Subtract from the signal: $d(t)=x(t)-m(t)$.
5. Replace x(t) with d(t) and iterate above steps until d(t) becomes a zero-mean process. After stopping the iteration, d(t) is the F-IMF denoted by $c_1(t)$.
6. Calculate the residue signal $r(t)=x(t)-c_1(t)$.
7. Repeat the above steps to obtain higher order IMF. The whole process is stopped when the final residual r(t) is a monotonic function.

Subsequently, the original signal x(t) is represented by $$x(t) = \sum_{i=1}^{n} c_i(t) + r(t), \quad (1)$$

where $c_i(t)$ is the i-th order IMF and $r(t)=c_{n+1}(t)$. As a result, the EMD module 114 can perform as a high-pass filter for $c_1(t)$ and a low-pass filter for $c_2(t)$. Furthermore, it has been determined that the F-IMF generated by the EMD module 114 may contain components corresponding to MN artifacts noise for any well sampled data. It should be understood by those skilled in the art that the F-IMF of clean ECG segment have periodic patterns whereas the MN artifact corrupted ECG signals or noisy ECG signals have highly varying irregular dynamics with lower magnitudes.

The real-time MN artifact detection application 110 further includes a square function module 116 that is configured to square the F-IMF generated by the EMD module 114. The purpose for squaring the F-IMF is to account for both the positive and negative values associated with the sum of the IMFs decomposed from the ECG signal. Furthermore, by squaring the F-IMFs, the difference in values can be further accentuated.

The application 110 may also include a scaling module 118 configured to scale the SF-IMF such that the maximum value is equal to one. In various embodiments, the scaling or normalizing is performed since the ECG signal values change according to subjects and channels related to lead combination. Accordingly, by normalizing the SF-IMF to a standardized scale, inconsistencies that may arise from subject to subject or due to varying lead combinations can be discounted and will further aid in identifying a consistent and optimum low level threshold value for all subjects. According to various embodiments, the scaling module 118 may also be configured to remove the top 5% of the squared F-IMFs prior to scaling. In this way, peaks that may have been formed due to artifacts that cannot be attributed to the subject can be discarded. For instance, it has been determined that F-IMFs may form unexpectedly large peaks due to abrupt changes in DC values detected during a ECG recording.

Upon scaling the SF-IMF, the scaling module 118 may be configured to extract the low level sequences (LLS), which lie in the range between 0 and $TH_{LLS}$, where $TH_{LLS}<1$. The low level sequences may be extracted to collect low amplitude data only, such as components having values between 0 mV and 100 mV as typical R peak amplitudes range between 100 mV and 500 mV. It has been determined that the R peaks of MN artifact corrupted ECG signals are not as clearly discernable as R peaks formed in clean ECG signals.

The real-time MN artifact detection application 110 further includes a Shannon Entropy (SE) calculation module 120 that calculates the SE to characterize randomness, a mean calculation module 122 that is configured to calculate the mean to quantify LLS level, and a root mean square of successive RR differences (RMSSD) calculation module 124 to quantify variability. The application further includes an ECG signal determination module 126 that utilizes the SE, mean, and RMSSD values to determine if the ECG signal is clean or noisy. Additional details regarding the real-time MN artifact detection application 110 and the process of detecting MN artifacts in an ECG signal in real-time are provided below.

In various embodiments, the method of real-time MN artifact detection may be described as a two stage process. The first stage involves the use of determining the first order intrinsic mode function (F-IMF) from the empirical mode decomposition (EMD) of an ECG signal. By doing so, MN artifacts can be isolated as they are largely concentrated in high frequencies. The second stage involves the use of statistical measures, including but not limited to the SE, mean, and RMSSD or variance, on the F-IMF time series to look for characteristics of randomness and variability. Utilizing the techniques disclosed herein, the presence of MN artifacts can be detected with sensitivity and specificity of at least 96.63% and 94.73%, respectively. Furthermore, the false positive detection of AF can be reduced from approximately 16.45% to 0% in subjects diagnosed with AF. In addition, the detection of MN artifacts does not adversely affect correctly-detected AF segments. Finally, the computation time to determine a MN artifact is less than 0.2 seconds, thereby allowing the techniques disclosed herein to be utilized for real-time Holter monitoring.

Embodiments of methods for automatically detecting motion artifact from ECG signals using empirical mode decomposition (EMD) and various statistical measures such as mean, variance, root mean square of successive difference (RMSSD) and Shannon Entropy (SE).

Figure 2:
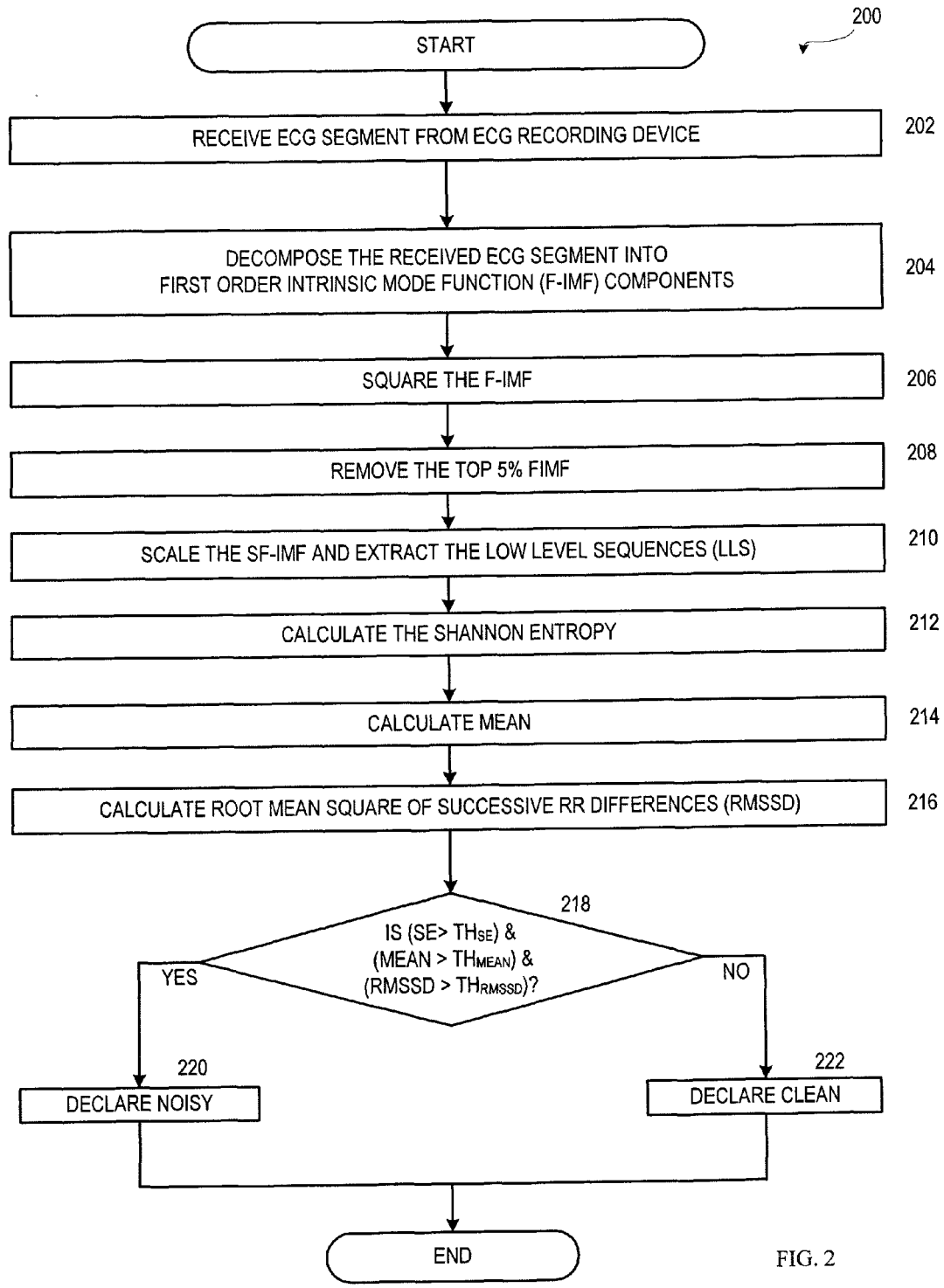
FIG. 2 is a logical flow diagram illustrating a method of detecting MN artifacts in a sample ECG segment according to embodiments of the present disclosure.

Referring now to FIG. 2, a logical flow diagram illustrating a method of detecting MN artifacts in a sample ECG segment according to embodiments of the present disclosure is shown. The routine 200 begins at operation 202, where the ECG reception module 112 receives an ECG segment that may or may not include MN artifacts. In various embodiments, the ECG segment can be received from a Holter monitor 150 or any other type of ECG recording device.

From operation 202, the routine 200 proceeds to operation 204, where the empirical mode decomposition module 114 decomposes the received ECG segment into first order intrinsic mode functions (F-IMFs) using empirical mode decomposition. The EMD operation can isolate high frequency components of the received ECG signal, which have been determined to contain most of the MN artifacts.

From operation 204, the routine 200 proceeds to operation 206, where the square function module 116 squares the F-IMF to generate a squared first order intrinsic mode function (SF-IMF). This operation is performed to account for both positive and negative values. From operation 206, the routine 200 proceeds to operation 208, where the scaling module 118 removes the top 5% of the SF-IMF. This may be done to eliminate peaks formed due to the abrupt change in DC values of an ECG segment. It has been determined that abrupt changes in DC values result in the creation of dominant peaks. As a result, the top 5% of the SF-IMF is removed to eliminate peaks that may have been generated by abrupt changes in DC values.

From operation 208, the routine 200 proceeds to operation 210, where the scaling module 118 scales the SF-IMF such that the maximum value is equal to one. In various embodiments, the scaling is done since the ECG signal values change according to subjects and channels related to lead combination. The scaling module may also extract the low level sequences (LLS).

From operation 210, the routine 200 proceeds to operation 212, where the Shannon Entropy calculation module 120 determines the Shannon Entropy of the extracted SF-IMFs to characterize randomness. Shannon Entropy provides a quantitative measure of uncertainty for a random variable. In particular, the SE provides quantitative information about the complexity of a signal. Complexity refers to the difficulty in describing or understanding a signal. It has been determined that the SE of normal sinus rhythm is significantly lower than AF.

From operation 212, the routine 200 proceeds to operation 214, where the mean calculation module 122 determines the mean to quantify LLS level. From operation 214, the routine 200 proceeds to operation 216, where the RMSSD calculation module 124 determines the RMSSD to quantify variability. Beat-to-beat variability is estimated by the root mean square of successive RR differences (RMSSD). Since AF exhibits higher variability between adjacent RR intervals than periodic rhythms such as sinus rhythm, the RMSSD is expected to be higher.

From operation 216, the routine 200 proceeds to operation 218, where the ECG signal determination module 126 determines if the determined Shannon Entropy, mean, and RMSSD are each greater than corresponding threshold values of $TH_{SE}$, $TH_{MEAN}$, and $TH_{RMSSD}$. Details regarding how the threshold values are determined are provided below with respect to FIGS. 5-8. If, at operation 218, the ECG signal determination module 126 determines that the determined Shannon Entropy, mean, and RMSSD are each greater than the corresponding threshold values, the routine 200 proceeds to operation 220, where the ECG signal determination module 126 determines that the ECG signal includes MN artifacts.

If, however, at operation 218, the ECG signal determination module 126 determines that any of the determined Shannon Entropy, mean, and RMSSD is not greater than the corresponding threshold, the routine 200 proceeds to operation 222, where the ECG signal determination module 126 determines that the ECG signal is clean and does not include MN artifacts.

Figure 3A:
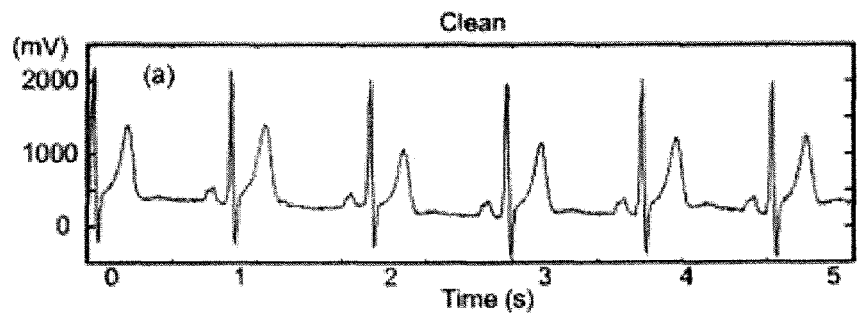
FIG. 3A illustrates a raw clean electrocardiogram (ECG) signal recorded by an ambulatory electrocardiography device according to embodiments of the present disclosure.
Figure 3B:
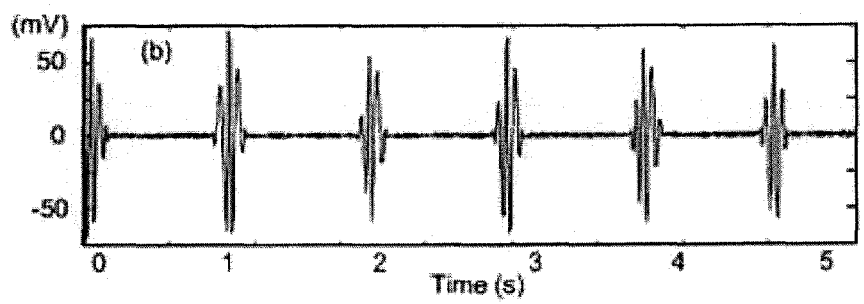
FIG. 3B illustrates a first order intrinsic mode function (F-IMF) associated with the raw ECG signal of FIG. 3A according to embodiments of the present disclosure.

FIG. 3A illustrates a raw clean electrocardiogram (ECG) signal recorded by an ambulatory electrocardiography device according to embodiments of the present disclosure. According to embodiments, the graph of FIG. 3A illustrates a sample raw clean ECG signal recorded by the Holter monitor 150. FIG. 3B illustrates a first order intrinsic mode function (F-IMF) associated with the raw ECG signal of FIG. 1A. As described above, the F-IMF shown in FIG. 3B can be generated by the empirical mode decomposition module 114 upon performing an EMD operation on the raw clean ECG signal shown in FIG. 3A.

Figure 3C:
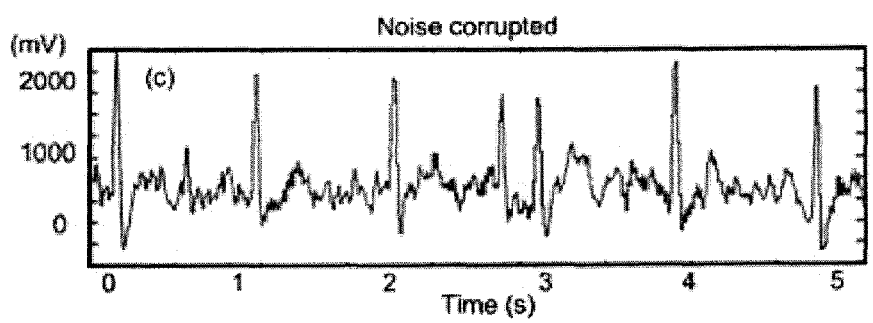
FIG. 3C illustrates a raw noisy ECG signal recorded by an ambulatory electrocardiography device according to embodiments of the present disclosure.
Figure 3D:
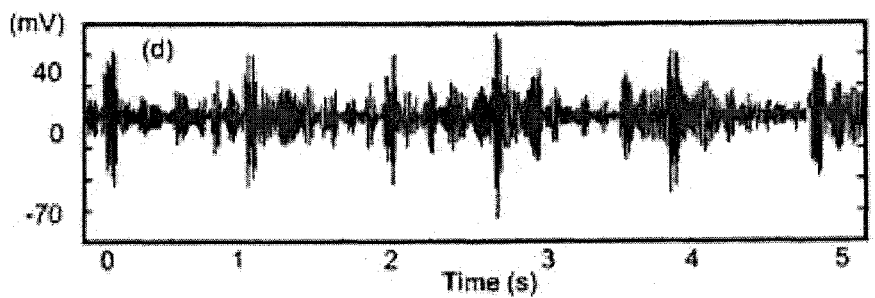
FIG. 3D illustrates a first order intrinsic mode function (F-IMF) associated with the raw ECG signal of FIG. 3C according to embodiments of the present disclosure.

FIG. 3C illustrates a raw noisy ECG signal recorded by an ambulatory electrocardiography device according to embodiments of the present disclosure. According to embodiments, the graph of FIG. 3C illustrates a sample raw ECG signal containing MN artifacts recorded by the Holter monitor 150. FIG. 3D illustrates a first order intrinsic mode function (F-IMF) associated with the raw ECG signal of FIG. 3C. Similar to the F-IMF shown in FIG. 3B, the F-IMF shown in FIG. 3D can also be generated by the empirical mode decomposition module 114 upon performing an EMD operation on the raw clean ECG signal shown in FIG. 3C.

Figure 4A:
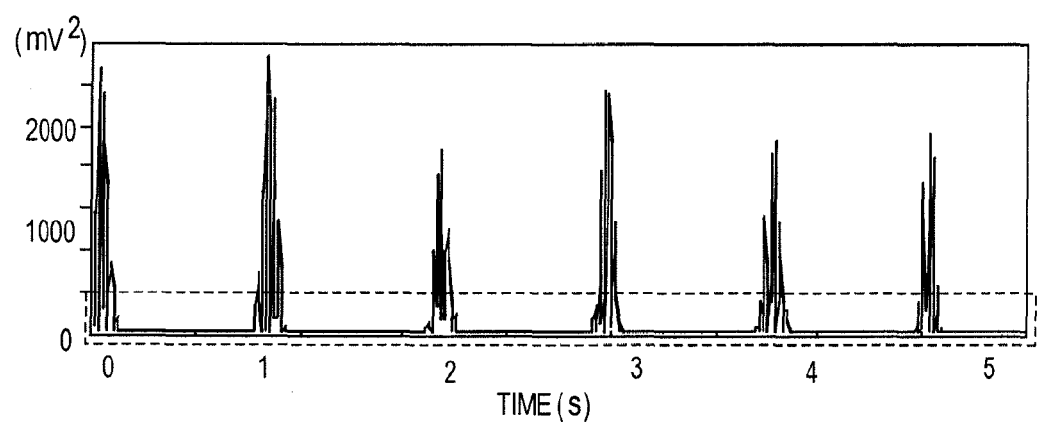
FIG. 4A illustrates a squared first order intrinsic mode function (SF-IMF) associated with the clean F-IMF of FIG. 3B according to embodiments of the present disclosure.
Figure 4B:
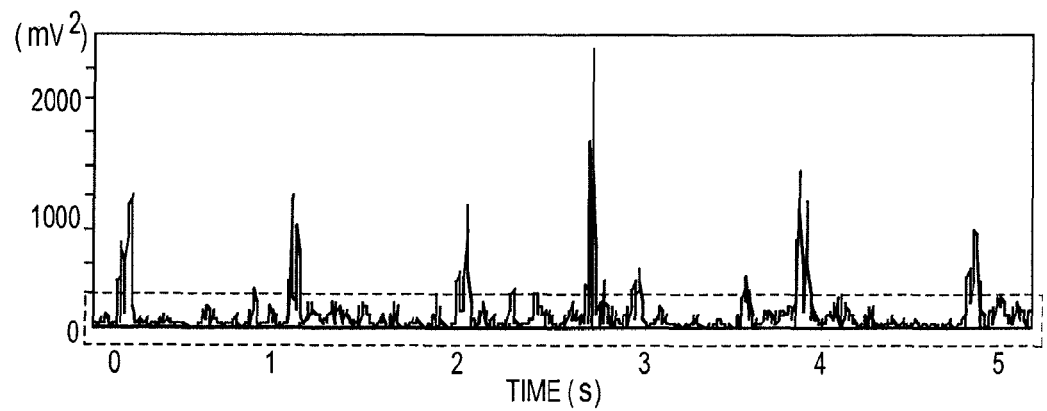
FIG. 4B illustrates a squared first order intrinsic mode function (SF-IMF) associated with the noisy F-IMF of FIG. 3D according to embodiments of the present disclosure.

FIG. 4A illustrates a squared first order intrinsic mode function (SF-IMF) associated with the clean F-IMF of FIG. 3B. As described above, the square function module 116 is configured to square the clean F-IMF shown in FIG. 3B to generate the SF-IMF shown in FIG. 4A. Similarly, FIG. 4B illustrates a squared first order intrinsic mode function (SF-IMF) associated with the noisy F-IMF of FIG. 3D. Again, the square function module 116 is configured to square the noisy F-IMF shown in FIG. 3D to generate the SF-IMF shown in FIG. 4B.

Figure 5A:
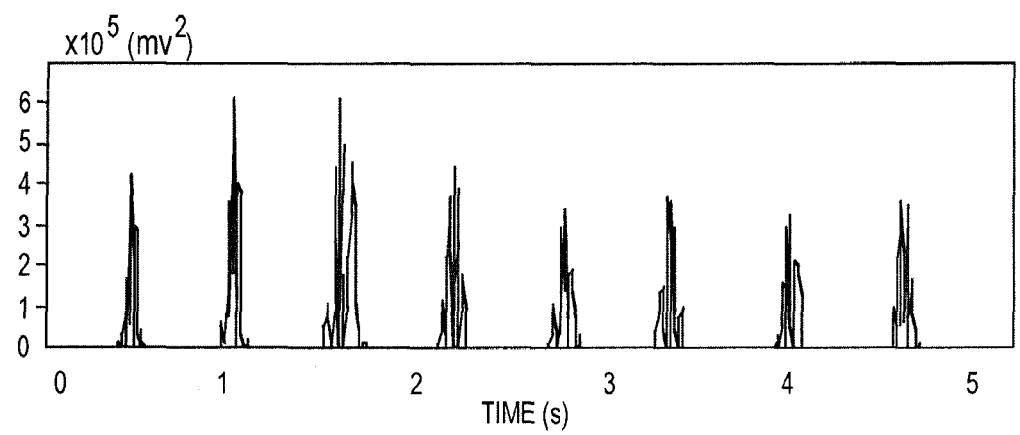
FIG. 5A illustrates an SF-IMF of a sample first subject having dominant peak values according to embodiments of the present disclosure.
Figure 5B:
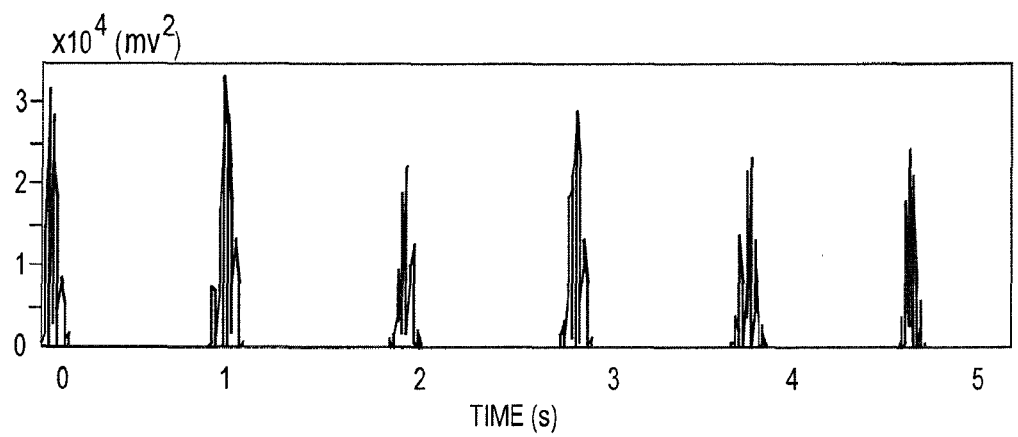
FIG. 5B illustrates an SF-IMF of a sample second subject having dominant peak values that is 20 times smaller than the dominant peak values associated with the SF-IMF of the sample first subject of FIG. 5A according to embodiments of the present disclosure.

Referring now to FIGS. 5A and 5B, graphs associated with SF-IMFs of two subjects is shown. The SF-IMF associated with the subject associated with FIG. 5A has dominant peak values that are twenty times greater than the dominant peak values that correspond to the SF-IMF associated with the subject associated with FIG. 5B. Therefore, by scaling the SF-IMF, a consistent and optimal low level threshold value for all subjects with any lead combination can be determined.

Figure 6A:
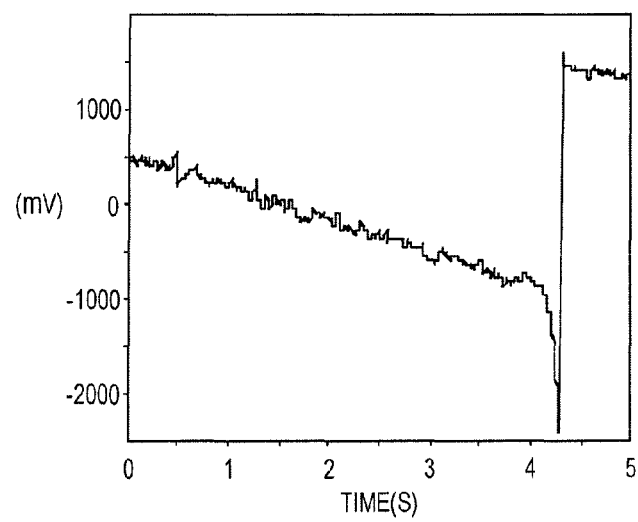
FIGS. 6A-C illustrate graphs showing that an abrupt change of DC value can lead to a spike in a scaled SF-IMF according to embodiments of the present disclosure.
Figure 6B:
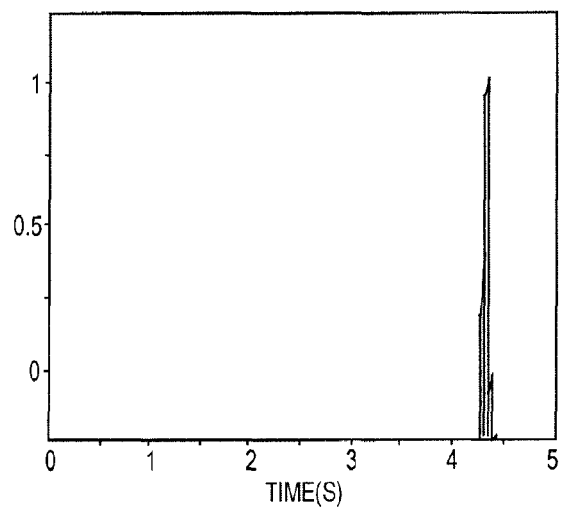
Figure 6C:
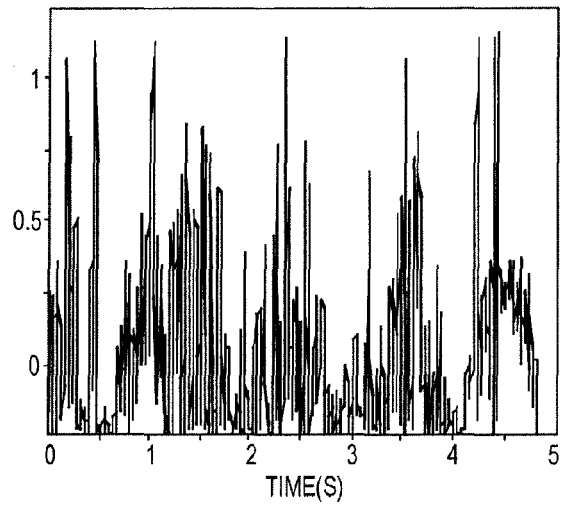

FIGS. 6A-C illustrate graphs showing that an abrupt change of DC value can lead to a spike in a scaled SF-IMF according to embodiments of the present disclosure. It has been determined that when the DC value of an ECG segment abruptly changes as indicated by the spike in FIG. 6A, a dominant peak is generated as a result of the spike, as shown in FIG. 6B. Since this spike is much larger than peaks generated due to MN artifacts, the scaling module 118 can be configured to remove the top 5% of the SF-IMF. In this way, a graph illustrating peaks associated with MN artifacts can be plotted to a more appropriate scale.

FIGS. 7A-F illustrate average, high 5% and high 95% (bottom 5%) values of Shannon Entropy (SE), mean and RMSSD according to $TH_{LLS}$ and each different mode of static, jogging, and tapping, according to embodiments of the present disclosure. According to embodiments, the values shown in FIGS. 7A-F are based on collected ECG recordings from 30 healthy subjects using the ScottCare RZ153 series recorders. The data was acquired at 180 samples per second with 10 bit resolution for 3 minutes. Among the 30 healthy subjects, 15 males and 15 females of age 24±3.1 years were involved. None of the subjects had cardiac diseases or related pathologies. During the recording, each subject was asked to stand without any movement for the first one minute. For the next one minute, each one was asked to jog. For the last one minute, each one was asked to tap one of electrodes. The last two minute ECG segment was corrupted by MN artifact while the first one minute segment was free of noise on the recording. Each data set was categorized into 'static', 'jogging' and 'tapping', and then analyzed for MN artifact presence and optimum threshold values using the application 110. The segment length used for data collection was 5 seconds.

As shown in the figures, FIG. 7A illustrates that the Shannon Entropy on the average of the static mode was remarkably lower than the other modes of jogging and tapping. FIG. 7D further illustrates that the top 5% of Shannon Entropy values associated with the static mode was lower than the bottom 5% of Shannon Entropy values associated with the jogging and tapping modes when the $TH_{LLS}$ was greater than 0.06 and less than 0.40. FIGS. 7B and 7C illustrate that the mean and the RMSSD values associated with the static mode are also remarkably lower than the corresponding mean and RMSSD values associated with the jogging and tapping modes. FIG. 7E illustrates that the top 5% of mean values associated with the static mode is less than the bottom 5% mean values associated with the jogging and tapping modes, when the $TH_{LLS}$ was greater than 0.08 and less than 0.28. Similarly, in FIG. 7F, the top 5% of the RMSSD values of the static mode is less than the bottom 5% of RMSSD values associated with the jogging and tapping modes when the $TH_{LLS}$ was greater than 0.02 and less than 0.32. As a result and based on the readings obtained in the embodiment described herein, the optimum $TH_{LLS}$ can be found approximately in the range between 0.08 and 0.28. Based on FIGS. 7A-F, a threshold value $TH_{LLS}$ that is too small may not be sufficient to collect MN artifacts with the scaled SF-IMF, while a threshold value $TH_{LLS}$ that is too large may include even real signal, which is undesirable.

Figure 8A:
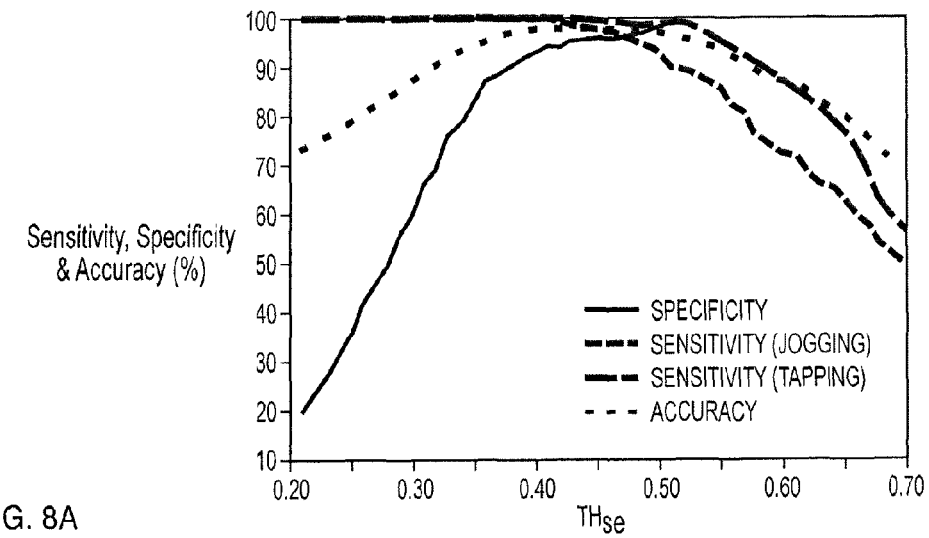
FIGS. 8A-C illustrate sensitivity, specificity and accuracy values according to SE, mean, and RMSSD thresholds, according to embodiments of the present disclosure.
Figure 8B:
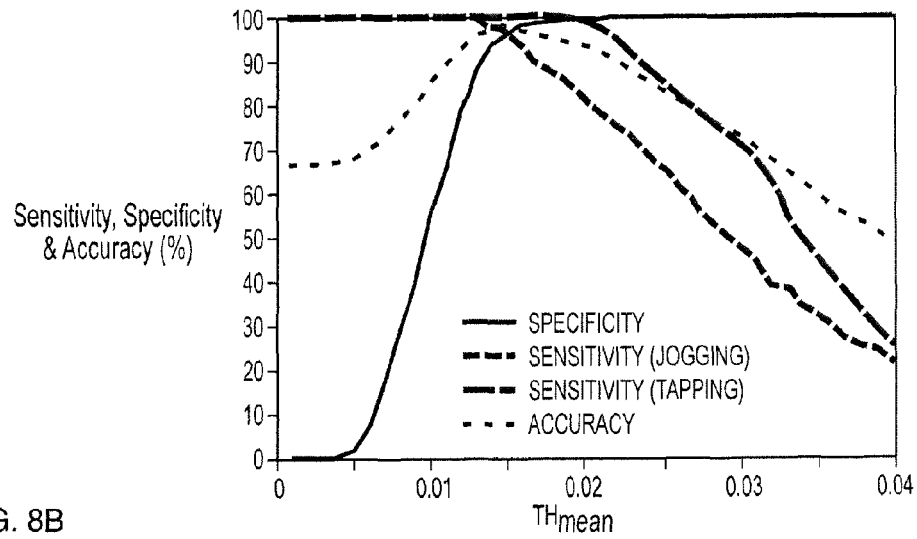
Figure 8C:
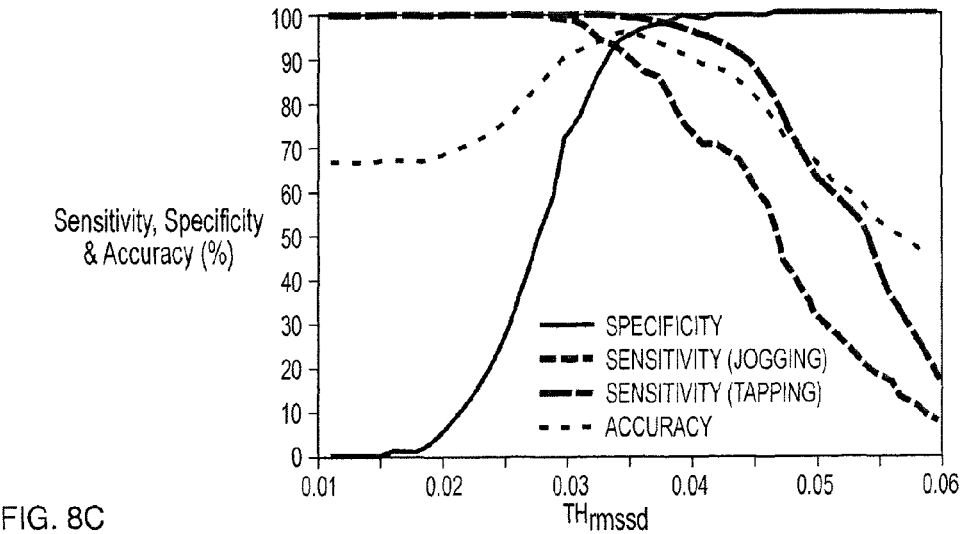

FIGS. 8A-C illustrate sensitivity, specificity and accuracy values according to Shannon Entropy, mean, and RMSSD thresholds, according to embodiments of the present disclosure. The specificity was calculated based on the 'static' mode data set. 5 second segments obtained from the 'static' mode data set declared as clean were counted towards the specificity. The sensitivity was calculated based on the two modes of 'jogging' and 'tapping'. Segments obtained from the jogging and tapping mode data sets that are declared noisy count towards the sensitivity. We calculated the accuracy by averaging the sensitivity and specificity. In particular, using a $TH_{LLS}$ value of 0.2, specificity, sensitivity, and accuracy regarding each threshold value of $TH_{SE}$, $TH_{MEAN}$, and $TH_{RMSSD}$ are plotted as shown in FIGS. 8A-C.

Figure 9A:
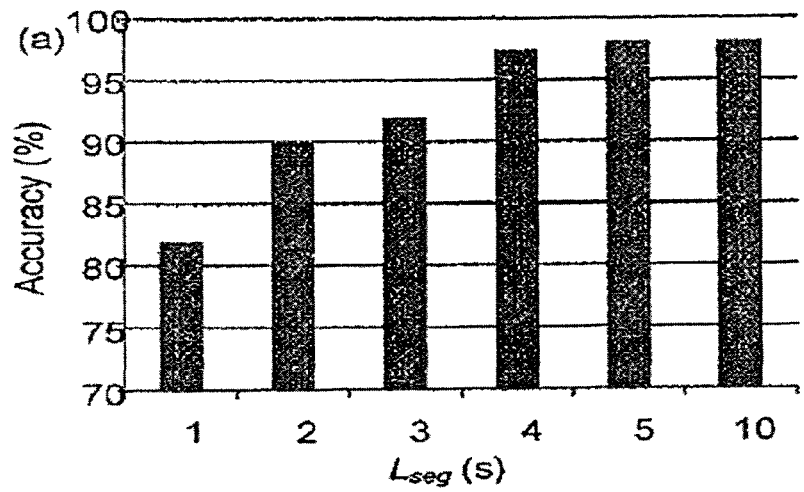
FIGS. 9A-C illustrate the relationship of segment length with accuracy, computation time with a clean segment, and computation time with a noisy segment, respectively according to embodiments of the present disclosure.
Figure 9B:
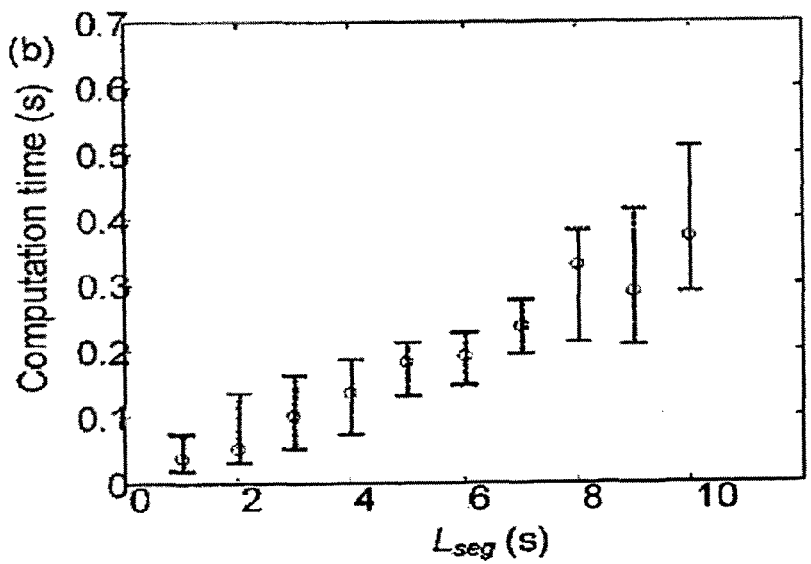
Figure 9C:
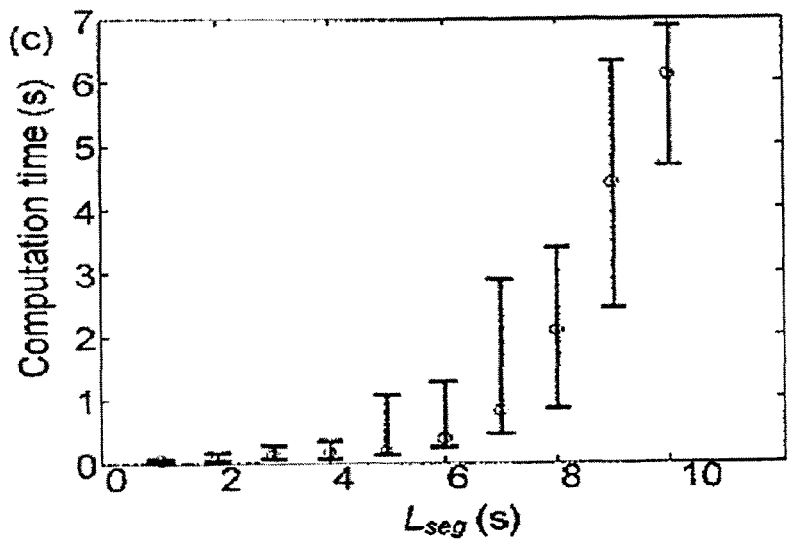

FIGS. 9A-C illustrate the relationship of segment length with accuracy, computation time with a clean segment, and computation time with a noisy segment, respectively according to embodiments of the present disclosure. In particular, FIG. 9A illustrates the accuracy for various segment lengths. It can be seen that the accuracy achieved by a segment length of 4 seconds is nearly as good as the accuracy achieved by a segment length of 10 seconds. FIG. 9B illustrates the computation times for various segment lengths of a clean segment. In particular, the computation time for a segment length of 10 seconds was more than twice the computation time for a segment length of 4 seconds. FIG. 9C illustrates the computation times for various segment lengths of a noisy segment. It is clear from the graph in FIG. 9C that the computation time for a segment length of 10 seconds was more than five times the computation time for a segment length of 4 seconds.

The analysis performed in FIGS. 9A-C may be used to determine the optimal segment length. Regarding the accuracy as shown in FIG. 9A, the accuracy is shown to be almost constant around 97~98% when the segment length is equal or longer than 4 seconds: 97.2%, 98.25% and 98.27% with 4, 5 and 10 second segments, respectively. Regarding the computational complexity, the computation time changed according to clean or noisy segment. As mentioned above, FIG. 9B shows the computation time taken to analyze a clean segment while FIG. 9C shows the computation time taken to analyze a noisy segment. With respect to the clean segment, the computation time increased linearly to the segment length. However, with respect to the noisy segment, the computational time increased sharply when the segment length exceeds over 6 seconds. As a result, it can be assumed that the optimum segment length can be found between 4 seconds and 6 seconds. In other embodiments, the optimum segment length may various to include segment lengths less than 4 seconds or greater than 6 seconds.

In an experiment conducted to evaluate the effect of the real-time motion and noise artifact detection system 100 disclosed herein, seven monitoring devices, each comprising 100,000 samples at 180 samples per second with 10 bit resolution (approximately 10 minutes) were used to provide ECG signals. All data recordings were collected using the ScottCare RZ153 series recorders. It should be appreciated that other types of recorders may be utilized without departing from the scope of the present disclosure. The data was taken from a wide variety of unknown subjects in which a false AF was reported to be detected for non-AF subjects. Utilizing the real-time MN artifact detection application 110, each 5 second segment of each data was analyzed and declared as clean or noisy. If the segment was declared to be noisy, the segment was discarded. Using the remaining segments of each data, RR intervals were extracted and analyzed for presence of AF rhythms.

Table I shows the results of the false AF detection before and after MN artifact elimination based on the seven data sets. In the Data I, the false AF was detected 172 times out of 745 RR intervals (RRIs). By using the MN artifact algorithm, 76.50% of segments were declared as noisy and discarded. AF was not detected in the remaining segments. Similarly, in the Data II thorough the Data VI, AF was not detected in any of the segments that remained after discarding the noisy segments. In the Data VII, the false AF was detected 511 times out of 1029 RRIs (49.66%) from the original data, and the false AF detection rate was reduced to 26.38% (143 out of 542 RRIs).

TABLE I

False AF detection rates before and after MN artifact elimination based on 7 data sets

| Data | False AF detection (rate) | | Elimination rate (MN artifact detection rate) |
|---|---|---|---|
| | w/ original segment | after MN artifact elimination | |
| I | 172/745 (23.09%) | 0/175 (0%) | 76.50% |
| II | 70/756 (9.26%) | 0/323 (0%) | 57.60% |
| III | 70/756 (13.62%) | 0/407 (0%) | 47.70% |
| IV | 10/686 (1.46%) | 0/537 (0%) | 20.70% |
| V | 98/992 (9.88%) | 0/724 (0%) | 25.44% |
| VI | 5/925 (0.54%) | 0/507 (0%) | 45.00% |
| VII | 511/1029 (49.66%) | 143/542 (26.38%) saturation 135 | 47.72% other waves detected 8 |

TABLE I-continued

In order to investigate the false AF detection from the Data VII, the segments that caused AF detection were analyzed and it was determined that the application failed to detect noisy segments when the ECG segment was saturated and when P and T waves have shapes that are similar to R peaks. In both cases, the LLS has smaller level, lower variability and less randomness when compared to the other noisy LLS.

Figure 10A:
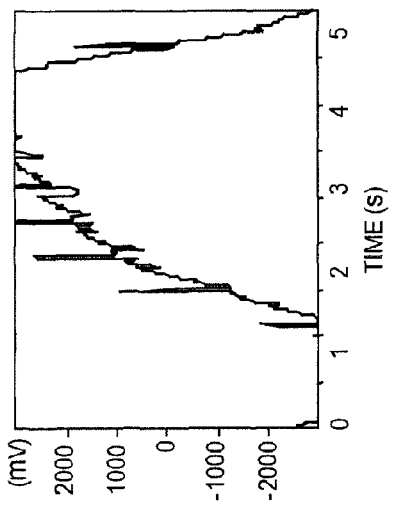
FIGS. 10A-F illustrate sample noisy segments that were not detected when the ECG segment was saturated and when the P and T waves shape similarly to R peaks according to embodiments of the present disclosure.
Figure 10B:
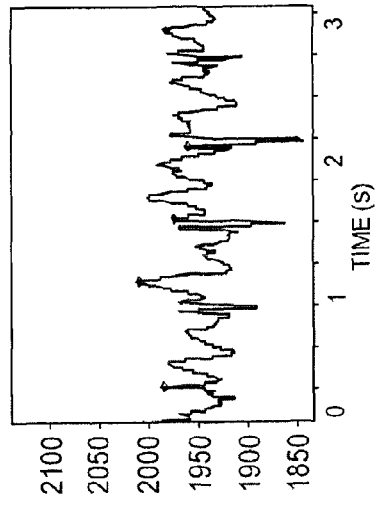
Figure 10C:
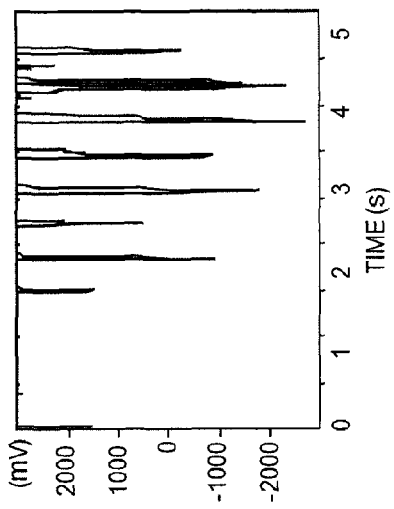
Figure 10D:
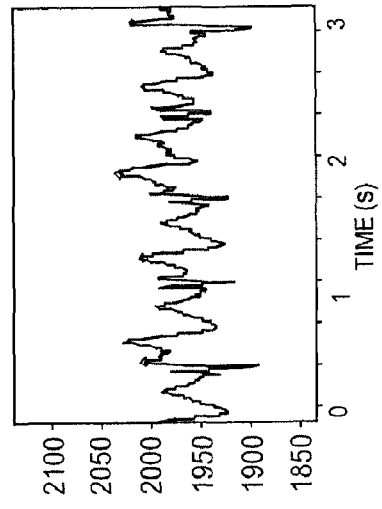
Figure 10E:
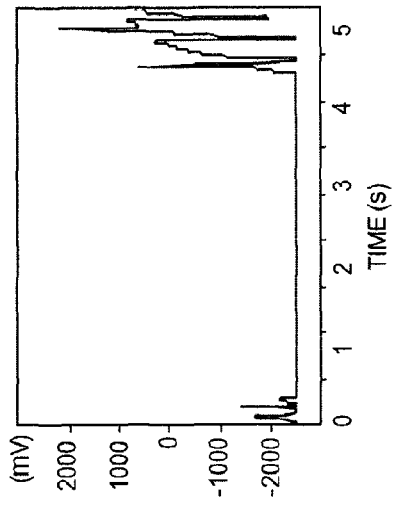
Figure 10F:
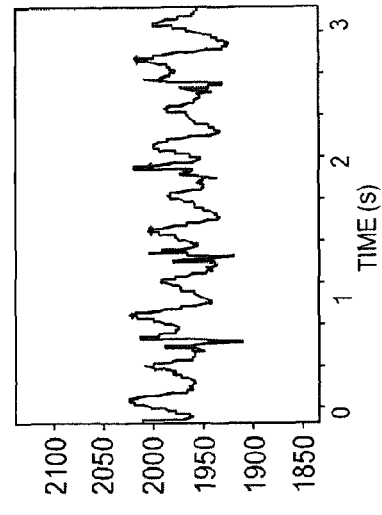

FIGS. 10A-F illustrate sample noisy segments that were not detected when the ECG segment was saturated and when the P and T waves shape similarly to R peaks according to embodiments of the present disclosure. In particular, FIGS. 10A-C show that the segment ECG values are saturated over or under ±2500 mV, which is the measurable range of a typical ScottCare RZ153 series recorder. FIGS. 10D-F show that the P and T waves that have shapes similar to R peaks led to incorrect R peaks being detected. In other words, both cases caused incorrect RRI extraction, which resulted in the presence of AF rhythms.

In various embodiments, segment disconnectivity may occur when a segment that is declared to be noisy is discarded, and the discontinued clean segment that remains is connected to another discontinued clean segment. By connecting them together, the LLS's randomness and variability may increase. In addition, RRIs may be biased to be a random sequence.

Figure 11:
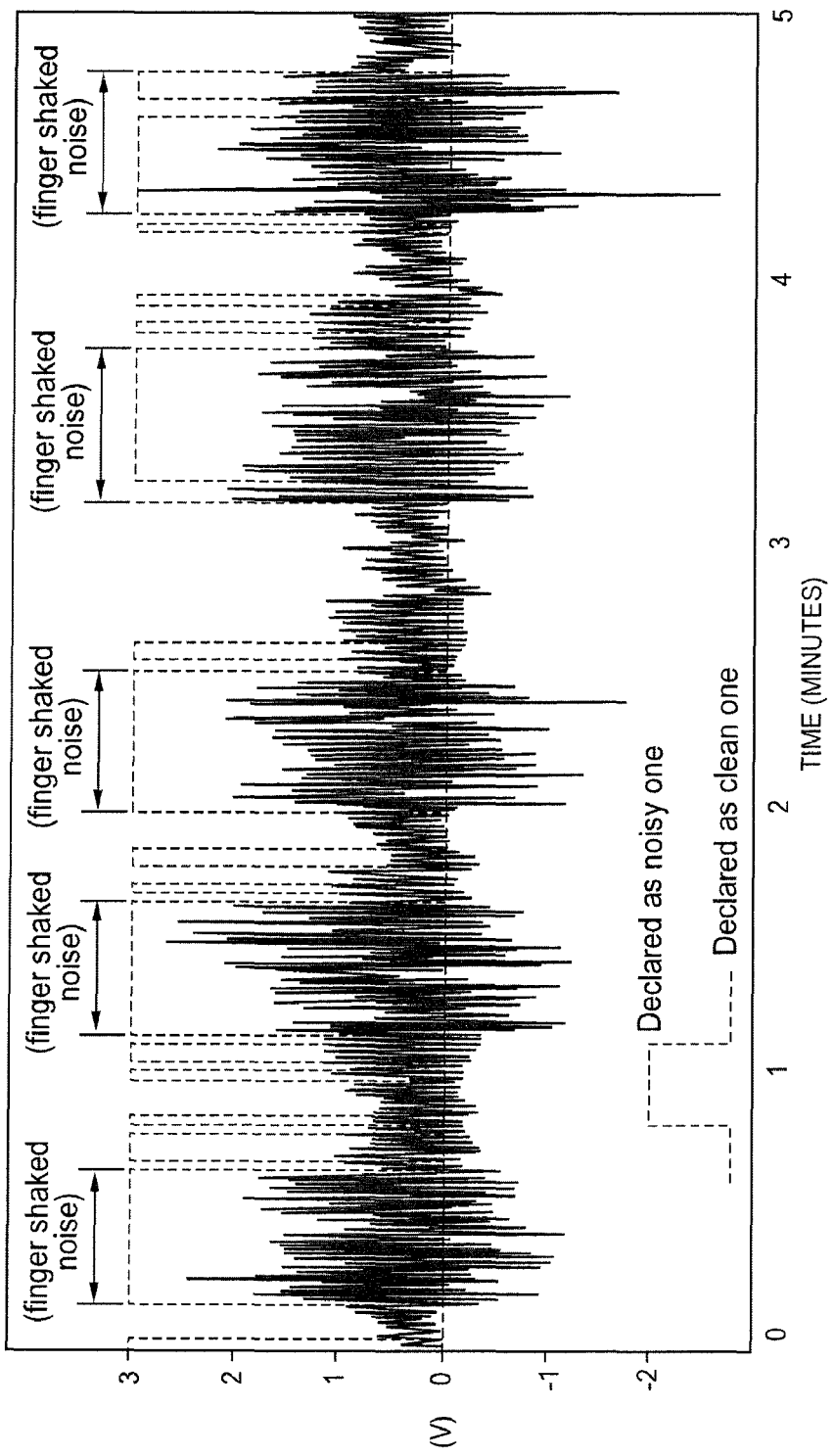
FIG. 11 illustrates a pulse oximeter recording showing the detection of MN artifacts according to embodiments of the present disclosure.

FIG. 11 illustrates a pulse oximeter recording showing the detection of MN artifacts according to embodiments of the present disclosure. In various embodiments, the pulse oximeter sensor may be implemented as a Nellcor Oximax MP506 of Boulder, Colo. According to the embodiment illustrated in FIG. 11, a subject had a pulse oximeter sensor attached to a finger. For a period of 5 minutes, the subject periodically made artificial MN artifacts by shaking his finger. More specifically, FIG. 11 shows the photoplethysmograph (PPG) wave (solid line) from the pulse oximeter sensor and its MN artifact detection results (dotted line). When the subject's finger had shaken, the MN artifact corrupted the PPG wave. The real-time MN artifact detection system analyzed the recording from the pulse oximeter sensor and performed with a sensitivity of 97.31% and a specificity of 73.33%. With further testing on additional subjects and monitoring devices, the sensitivity and specificity will increase.

Figure 12:
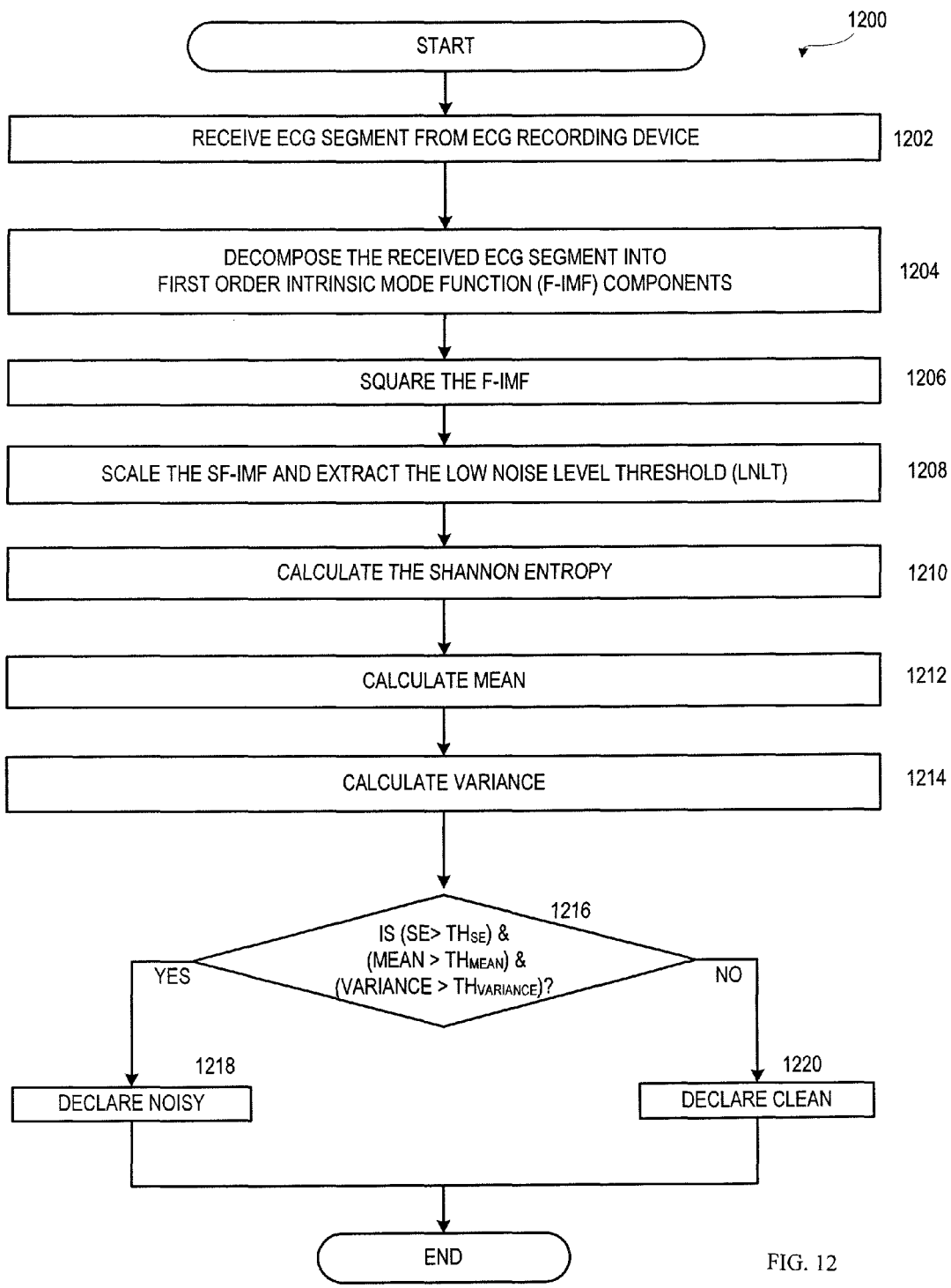
FIG. 12 is a logical flow diagram illustrating a method of detecting MN artifacts in a sample ECG segment according to embodiments of the present disclosure.

Referring now to FIG. 12, a logical flow diagram illustrating an alternate method of detecting MN artifacts in a sample ECG segment according to embodiments of the present disclosure is shown. The routine 1200 is similar to the routine 200 described above with respect to FIG. 2. The routine 1200 begins at operation 1202, where the ECG reception module 112 receives an ECG segment that may or may not include MN artifacts. In various embodiments, the ECG segment can be received from a Holter monitor 150 or any other type of ECG recording device.

From operation 1202, the routine 1200 proceeds to operation 1204, where the empirical mode decomposition module 114 decomposes the received ECG segment into first order intrinsic mode function (F-IMF) components using EMD. The EMD operation can isolate high frequency components of the received ECG signal, which have been determined to contain most of the MN artifacts' dynamics.

From operation 1204, the routine 1200 proceeds to operation 1206, where the square function module 116 squares the F-IMF to generate a squared first order intrinsic mode function (SF-IMF). This operation is performed to account for both positive and negative values. From operation 1206, the routine 1200 proceeds to operation 1208, where the scaling module 118 scales or normalizes the SF-IMF such that the maximum value is equal to one. In various embodiments, the scaling is done since the ECG signal values change according to subjects and channels related to lead combination.

In contrast to the routine 200 in which the scaling module 118 may extract low level sequences, the scaling module 118 may extract the low noise level threshold (LNLT) with respect to routine 1200. With a normalized squared-IMF, the scaling module 118 can determine the optimum low noise level threshold (LNLT) value denoted by $TH_{LNLT}$, which satisfies the following three statistical indices: Shannon Entropy (SE) to characterize randomness, a mean value to quantify LNLT level, and variance to quantify variability.

From operation 1208, the routine 1200 proceeds to operation 1210, where the Shannon Entropy calculation module 120 determines the Shannon Entropy to characterize randomness. From operation 1210, the routine 1200 proceeds to operation 1212, where the mean calculation module 122 determines the mean to quantify the low noise level threshold level. From operation 1212, the routine 1200 proceeds to operation 1214, where a variance calculation module (not shown) determines the variance to quantify variability.

From operation 1214, the routine 1200 proceeds to operation 1216, where the ECG signal determination module 126 determines if the determined Shannon Entropy, mean, and variance are each greater than a corresponding threshold. If, at operation 1216, the ECG signal determination module 126 determines that the determined Shannon Entropy, mean, and variance are each greater than the corresponding threshold, the routine 1200 proceeds to operation 1218, where the ECG signal determination module 126 indicates that the ECG signal includes MN artifacts.

If, however, at operation 1216, the ECG signal determination module 126 determines that any of the determined Shannon Entropy, mean, and variance is not greater than the corresponding threshold, the routine 1200 proceeds to operation 1220, where the ECG signal determination module 126 indicates that the ECG signal is clean and does not include MN artifacts. From operation 1218 and 1220, the routine 1200 ends.

Once $TH_{LNLT}$ and the thresholds for maximum sensitivity and specificity are determined for each of the three statistic values ($TH_{SE}$, $TH_{MEAN}$ and $TH_{VAR}$) using the receiver-operator characteristic (ROC) curve analysis, no further heuristic tuning for the threshold values may be required. In various embodiments, the same threshold values can be used for all subjects' data henceforth.

The ROC analysis was used to find $T_{HLNLT}$, $L_{SEG}$, $TH_{SE}$, $TH_{MEAN}$ and $TH_{VAR}$ for the optimum sensitivity and specificity. That is, the threshold parameters search can be considered by the following optimization problem:

1. LNLT level $TH_{LNLT}$ varied from 0 to 1 at intervals of 0.05.
2. Segment length $L_{SEG}$ varied from 1 (s) to 10 (s) at intervals of 1 (s).
3. SE threshold $TH_{SE}$ varied from 0 to 1 at intervals of 0.0001.
4. mean threshold $TH_{MEAN}$ varied from 0 to 1 at intervals of 0.0001.
5. variance threshold $TH_{VAR}$ varied from 0 to 0.1 at intervals of 0.00001.

A 5-element vector of the threshold parameter can be defined as $$\alpha = [T_{HLNLT}, L_{SEG}, TH_{SE}, TH_{MEAN}, TH_{VAR}]. \quad (2)$$

The elements of the vector parameter α are varied according to the ranges defined above. For each particular value of the vector $\alpha_k$, we find the number of True Positives ($TP_k$), True Negatives ($TN_k$), False Positives ($FP_k$) and False Negatives ($FN_k$) associated with the MN artifact detection. We use the sensitivity $TP_k/(TP_k+FN_k)$ and specificity $TN_k/(TN_k+FP_k)$ metrics in order to quantify accuracy of the MN artifact detection for the vector parameter $\alpha_k$. Also, we use the accuracy ($A_k$) by averaging the sensitivity and specificity.

Figure 13:
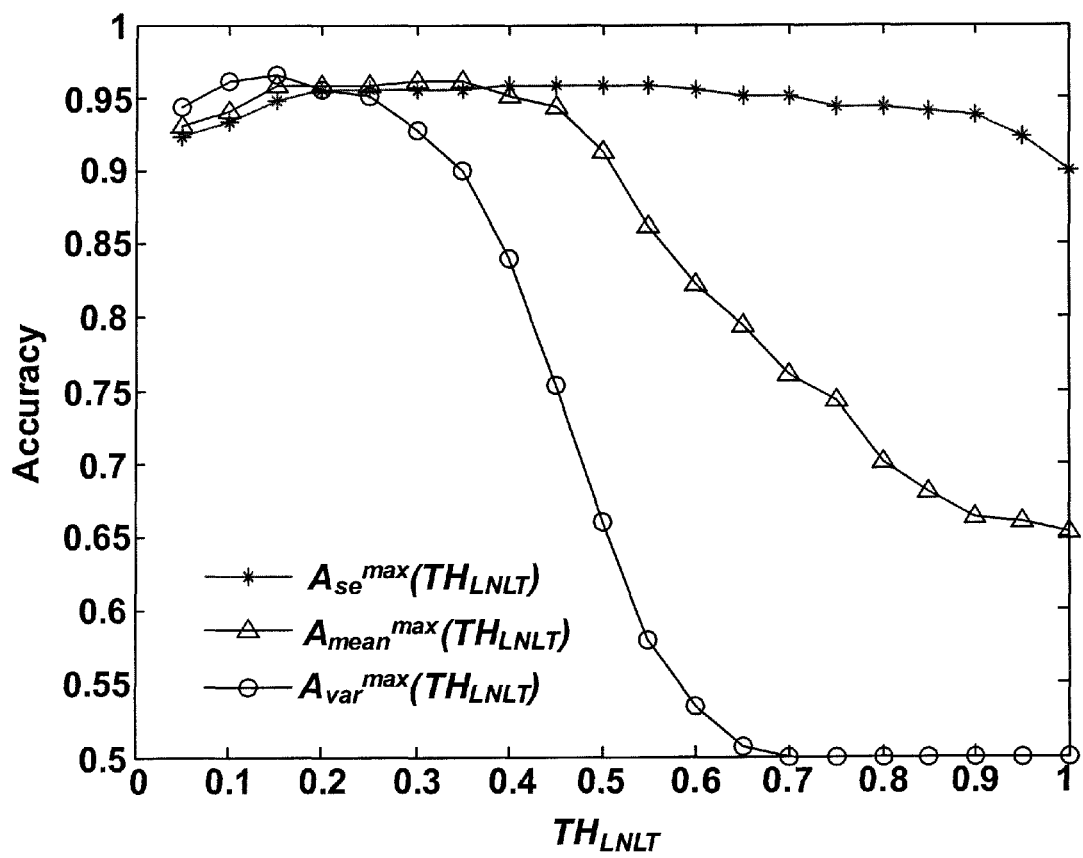
FIG. 13 illustrates graphs representing the accuracies of $A_{se}^{max}(TH_{LNLT})$, $A_{mean}^{max}(TH_{LNLT})$ and $A_{var}^{max}(TH_{LNLT})$ according to $TH_{SE}$, $TH_{MEAN}$, $TH_{VAR}$, and $TH_{LNLT}$ in accordance with the present disclosure.

Referring now to FIG. 13, graphs representing the accuracies of $A_{se}^{max}(TH_{LNLT})$, $A_{mean}^{max}(TH_{LNLT})$ and $A_{var}^{max}(TH_{LNLT})$ according to $TH_{SE}$, $TH_{MEAN}$, $TH_{VAR}$, and $TH_{LNLT}$ are shown. The $A_{se}^{max}(TH_{LNLT})$, $A_{mean}^{max}(TH_{LNLT})$ and $A_{var}^{max}(TH_{LNLT})$ were 0.9549, 0.9583 and 0.9618, where SE with $TH_{SE}$=0.5998; mean with $TH_{MEAN}$=0.0236; variance with $TH_{VAR}$=0.00082.

The α values for the optimum low noise level, segment length, SE, mean, and variance threshold values for data described above was found to be the following:

$$\alpha_{opt} = [0.20, 5, 0.5998, 0.0236, 0.00082] \quad (3)$$

Using the $\alpha_{opt}$ values, the sensitivity, specificity and accuracy is calculated to be 0.9549, 0.9792 and 0.9688, respectively. The optimization parameter is a 5-dimensiondal vector, thus, it is difficult to plot the accuracy metrics as a function of all the elements of the vector. As can be seen in FIG. 13, the value of 0.2 for $TH_{LNLT}$ provides the optimal accuracy for all three metrics. In estimating these accuracy values, we started by examining the Shannon Entropy according to the following:

$$A_{LNLT,se}^{max} = \arg_{TH_{LNLT} \in \{0.05\ 0.1\ \ldots\ 1\}} \max(A_{se}^{max}(TH_{LNLT})) \quad (4)$$

where $A_{LNLS,se}^{max}$ is the maximum accuracy value with the optimum $TH_{se}$ and $TH_{LNLT}$, $A_{se}^{max}(TH_{LNLT})$=arg max$_{TH_{se} \in \{0.001\ 0.002\ \ldots\ 1\}}(A(TH_{se}, T_{LNLT}))$, and $A_{se}^{max}(TH_{se}, T_{LNLT})$ is the set of accuracy values according to $TH_{LNLT}$ and $TH_{SE}$ that we considered. $A_{se}^{max}(TH_{LNLT})$ is the set of accuracy values according to $TH_{LNLT}$ given the maximum accuracies with the optimum $TH_{se}$. Similarly, $A_{LNLT,mean}^{max}$ and $A_{LNLT,var}^{max}$ were found for mean and variance.

In addition, it was found that $A_{LNLT,se}^{max}$=0.9549 with $TH_{se}$=0.5998, $A_{LNLT,mean}^{max}$=0.9583 with $TH_{mean}$=0.0236, and $A_{LNLT,var}^{max}$=0.9618 with $TH_{var}$=0.00082. By combining the three statistical values, the accuracy was found to be 0.9688.

Elements and components described herein may be further divided into additional components or joined together to form fewer components for performing the same functions.

Each computer program may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable media include, for example, a floppy disk, a flexible disk, hard disk, magnetic tape, or any other magnetic medium, a CDROM, any other optical medium, any physical medium with patterns of holes, a RAM, a PROM, and EPROM, a FLASH-EPROM, any other memory chip or cartridge, all of which are non-transitory. As stated in the USPTO 2005 Interim Guidelines for Examination of Patent Applications for Patent Subject Matter Eligibility, 1300 Off. Gaz. Pat. Office 142 (Nov. 22, 2005), "On the other hand, from a technological standpoint, a signal encoded with functional descriptive material is similar to a computer-readable memory encoded with functional descriptive material, in that they both create a functional interrelationship with a computer. In other words, a computer is able to execute the encoded functions, regardless of whether the format is a disk or a signal."

Although the teachings have been described with respect to various embodiments, it should be realized these teachings are also capable of a wide variety of further and other embodiments within the spirit and scope of the appended claims.

What is claimed is:

1. A method for detecting motion and noise artifacts in an electrocardiogram (ECG) recording, comprising:
    receiving an ECG segment;
    decomposing the received ECG segment into a sum of intrinsic mode functions;
    isolating intrinsic mode functions associated with motion and noise artifacts present within the ECG segment;
    determining randomness and variability characteristic values associated with the isolated intrinsic mode functions;
    comparing the randomness and variability characteristic values to threshold randomness and variability characteristic values; and
    determining that the received ECG segment includes motion and noise artifacts if the randomness and variability characteristic values exceed the threshold randomness and variability characteristic values.

2. The method of claim 1, wherein the ECG segment is recorded by an ambulatory ECG recording device.

3. The method of claim 1, wherein decomposing the received ECG segment into a sum of intrinsic mode functions comprises performing empirical mode decomposition (EMD) on the received ECG segment.

4. The method of claim 1, wherein isolating intrinsic mode functions associated with motion and noise artifacts present within the ECG segment further comprises:
    identifying first order intrinsic mode functions;
    squaring the identified first order intrinsic mode functions; and
    normalizing the squared first order intrinsic mode functions.

5. The method of claim 4, further comprising discarding squared first order intrinsic mode functions that have peaks that exceed a predefined threshold value.

6. The method of claim 4, further comprising extracting the low level sequences from the normalized squared first order intrinsic mode functions.

7. The method of claim 4, further comprising extracting the low noise level threshold sequences from the normalized squared first order intrinsic mode function components.

8. The method of claim 1, wherein determining randomness and variability characteristic values associated with the first order intrinsic mode function components of the received ECG segment comprises determining a Shannon Entropy, a mean, and a root mean square of successive RR differences (RMSSD) of extracted components of the received ECG segment.

9. The method of claim 8, wherein comparing the randomness and variability characteristics to threshold randomness and variability characteristic values comprises comparing the determined Shannon Entropy, mean, and RMSSD to threshold values of Shannon Entropy, mean, and RMSSD, respectively.

10. The method of claim 1, wherein determining randomness and variability characteristic values associated with the first order intrinsic mode function components of the received ECG segment comprises determining a Shannon Entropy, a mean, and a root mean square of successive RR differences (RMSSD) of extracted components of the received ECG segment.

11. The method of claim 10, wherein comparing the randomness and variability characteristics to threshold randomness and variability characteristic values comprises comparing the determined Shannon Entropy, mean, and variance to threshold values of Shannon Entropy, mean, and variance, respectively.

12. A system for detecting motion and noise artifacts in an electrocardiogram (ECG) recording, comprising:
    a processor;
    a memory; and
    a real-time motion and noise artifact detection application, comprising:
        an ECG reception module that receives an ECG segment,
        an empirical mode decomposition module that decomposes the received ECG segment into a sum of intrinsic mode functions,
        a signal processing module that isolates intrinsic mode functions associated with motion and noise artifacts present within the ECG segment,
        at least one characteristic calculation module that determines randomness and variability characteristic values associated with the isolated intrinsic mode functions, and
        a ECG determination module that compares randomness and variability characteristic values to threshold randomness and variability characteristic values and determines that the received ECG segment includes motion and noise artifacts if the randomness and variability characteristic values exceed the threshold randomness and variability characteristic values.

13. The system of claim 12, wherein the ECG reception module receives ECG signals from an electrocardiogram recording device.

14. The system of claim 12, wherein the signal processing module that isolates intrinsic mode functions associated with motion and noise artifacts present within the ECG segment comprises:
    an identification module that identifies first order intrinsic mode functions
    a squaring module that squares the identified first order intrinsic mode functions; and
    a scaling module that normalizes the squared first order intrinsic mode functions.

15. The system of claim 12, wherein the at least characteristic calculation module comprises:
a Shannon Entropy calculation module that calculates a Shannon Entropy of the isolated intrinsic mode functions;
a mean calculation module that calculates a mean of the isolated intrinsic mode functions; and
a RMSSD calculation module that calculates a RMSSD of the isolated intrinsic mode functions.

16. The system of claim 12, wherein the at least characteristic calculation module comprises:
a Shannon Entropy calculation module that calculates a Shannon Entropy of the isolated intrinsic mode functions;
a mean calculation module that calculates a mean of the isolated intrinsic mode functions; and
a variance calculation module that calculates a variance of the isolated intrinsic mode functions.

17. A computer-readable non-transitory storage medium, having computer-executable instructions stored thereon, which when executed by a processor, cause the computer to:
receive an ECG segment;
decompose the received ECG segment into a sum of intrinsic mode functions;
isolate intrinsic mode functions associated with motion and noise artifacts present within the ECG segment;
determine randomness and variability characteristic values associated with the isolated intrinsic mode functions;
compare the randomness and variability characteristic values to threshold randomness and variability characteristic values; and
determine that the received ECG segment includes motion and noise artifacts if the randomness and variability characteristic values exceed the threshold randomness and variability characteristic values.

18. The computer-readable non-transitory storage medium of claim 17, wherein decomposing the received ECG segment into a sum of intrinsic mode functions comprises performing empirical mode decomposition (EMD) on the received ECG segment.

19. The computer-readable non-transitory storage medium of claim 17, wherein isolating intrinsic mode functions associated with motion and noise artifacts present within the ECG segment further comprises:
identifying first order intrinsic mode functions;
squaring the identified first order intrinsic mode functions; and
normalizing the squared first order intrinsic mode functions.

20. The computer-readable non-transitory storage medium of claim 19, further comprising discarding squared first order intrinsic mode functions that have peaks that exceed a predefined threshold value.

21. The computer-readable non-transitory storage medium of claim 19, further comprising extracting the low level sequences from the normalized squared first order intrinsic mode functions.

22. The computer-readable non-transitory storage medium of claim 19, further comprising extracting the low noise level threshold sequences from the normalized squared first order intrinsic mode function components.

23. The computer-readable non-transitory storage medium of claim 17, wherein determining randomness and variability characteristic values associated with the first order intrinsic mode function components of the received ECG segment comprises determining a Shannon Entropy, a mean, and a root mean square of successive RR differences (RMSSD) of extracted components of the received ECG segment.

24. The computer-readable non-transitory storage medium of claim 23, wherein comparing the randomness and variability characteristics to threshold randomness and variability characteristic values comprises comparing the determined Shannon Entropy, mean, and RMSSD to threshold values of Shannon Entropy, mean, and RMSSD, respectively.

25. The computer-readable non-transitory storage medium of claim 17, wherein determining randomness and variability characteristic values associated with the first order intrinsic mode function components of the received ECG segment comprises determining a Shannon Entropy, a mean, and a root mean square of successive RR differences (RMSSD) of extracted components of the received ECG segment.

26. The computer-readable non-transitory storage medium of claim 25, wherein comparing the randomness and variability characteristics to threshold randomness and variability characteristic values comprises comparing the determined Shannon Entropy, mean, and variance to threshold values of Shannon Entropy, mean, and variance, respectively.

* * * * *